(12) United States Patent
Boehmer et al.

(10) Patent No.: US 7,923,396 B2
(45) Date of Patent: Apr. 12, 2011

(54) HYDROCARBON CONVERSION

(75) Inventors: Ingrid Boehmer, Forchheim (DE); M. Bruce Welch, Bartlesville, OK (US); Roland Schmidt, Bartlesville, OK (US); Bruce B. Randolph, Bartlesville, OK (US); Helmut G. Alt, Bayreuth (DE)

(73) Assignee: ConocoPhillips Company, Houston, TX (US)

( * ) Notice: Subject to any disclaimer, the term of this patent is extended or adjusted under 35 U.S.C. 154(b) by 1961 days.

(21) Appl. No.: 10/866,627

(22) Filed: Jun. 12, 2004

(65) Prior Publication Data

US 2005/0274647 A1    Dec. 15, 2005

(51) Int. Cl.
*B01J 29/06*    (2006.01)

(52) U.S. Cl. .......................................... 502/60; 502/74

(58) Field of Classification Search .............. 502/60, 502/74
See application file for complete search history.

(56) References Cited

U.S. PATENT DOCUMENTS

| | | | |
|---|---|---|---|
| 2,848,377 | A | 8/1958 | Webb |
| 3,291,855 | A | 12/1966 | Haensel |
| 3,439,061 | A | 4/1969 | Henderson et al. |
| 3,461,183 | A | 8/1969 | Hepp et al. |
| 3,487,112 | A | 12/1969 | Paulik et al. |
| 3,524,898 | A | 8/1970 | Beime et al. |
| 3,531,543 | A | 9/1970 | Clippinger et al. |
| 3,538,174 | A | 11/1970 | Brodbeck |
| 3,597,348 | A | 8/1971 | Boume et al. |
| 3,637,878 | A | 1/1972 | Hansford et al. |
| 3,726,809 | A | 4/1973 | Allum et al. |
| 3,733,362 | A | 5/1973 | Biale |
| 3,763,255 | A | 10/1973 | Hayes |
| 3,871,996 | A | 3/1975 | Sinfelt |
| 3,992,323 | A | 11/1976 | Yoo et al. |
| 4,021,502 | A | 5/1977 | Plank et al. |
| 4,044,066 | A | 8/1977 | Ripley |
| 4,056,576 | A | 11/1977 | Gregory et al. |
| 4,070,413 | A | 1/1978 | Imai |
| 4,191,846 | A | 3/1980 | Farha, Jr. et al. |
| 4,219,689 | A | 8/1980 | Murtha .......................... 585/425 |
| 4,442,040 | A | 4/1984 | Panster et al. |
| 4,458,098 | A | 7/1984 | Antos |
| 4,463,104 | A | 7/1984 | Antos et al. |
| 4,532,225 | A * | 7/1985 | Tsao et al. ....................... 502/62 |
| 4,654,461 | A | 3/1987 | Drake et al. |
| 4,727,216 | A | 2/1988 | Miller ............................ 585/660 |
| 4,927,521 | A | 5/1990 | Chu ................................ 208/65 |
| 4,940,684 | A | 7/1990 | Okutani et al. |
| 4,996,387 | A | 2/1991 | Gerhold et al. |
| 5,012,008 | A | 4/1991 | Drago et al. |
| 5,077,447 | A | 12/1991 | Miller et al. |
| 5,220,093 | A | 6/1993 | Gartside et al. |
| 5,233,121 | A | 8/1993 | Modica .......................... 585/739 |
| 5,346,871 | A | 9/1994 | Robbins et al. |
| 5,430,220 | A | 7/1995 | Khare et al. |
| 5,436,383 | A | 7/1995 | Le Peltier et al. |
| 5,439,859 | A | 8/1995 | Durante et al. |
| 5,731,255 | A | 3/1998 | Pan et al. |
| 6,022,936 | A | 2/2000 | Tamao et al. |
| 6,184,409 | B1 | 2/2001 | Patel et al. |
| 6,187,985 | B1 | 2/2001 | Le Peltier et al. |
| 6,235,910 | B1 | 5/2001 | Beller et al. |

OTHER PUBLICATIONS

USPTO Office Action dated Apr. 4, 2007 for U.S. Appl. No. 10/866,158, filed Jun. 12, 2004; Inventor: Ingrid Boehmer; Assignee: ConocoPhillips Company; 11 pages.

* cited by examiner

*Primary Examiner* — Elizabeth D Wood

(57) ABSTRACT

A catalyst comprising at least one metal selected from the group consisting of Group 8 metals, Group 9 metals, Group 10 metals and combinations thereof, an organic compound, and a solid acid and a method of making said catalyst is disclosed. The catalyst can be used in a hydrocarbon conversion process.

1 Claim, No Drawings

HYDROCARBON CONVERSION

This invention relates to the conversion of hydrocarbons. More particularly, this invention relates to the conversion of hydrocarbons in the presence of an organometallic complex on a solid acid support component.

BACKGROUND OF THE INVENTION

Regulations in future motor fuel specifications are expected to continue the trend of reducing the amount of volatile $C_4$ and $C_5$ paraffins present in gasoline. However, $C_4$ and $C_5$ paraffins are relatively unreactive and have no functional groups with which chemical transformations can be made. Therefore, strong acid catalysts or activation with organometallic reagents are the possible routes to conversion.

SUMMARY OF THE INVENTION

It is thus an object of the present invention to provide a novel composition.

It is yet another object of the present invention to provide a process for the conversion of hydrocarbon feedstocks.

In accordance with the present invention, the inventive composition comprises, consists of, or consists essentially of:
a) at least one metal selected from the group consisting of Group 8 metals, Group 9 metals, Group 10 metals, and combinations thereof,
b) a cyclooctadiene; and
c) beta zeolite.

The second embodiment of the present invention includes a novel method comprising, consisting of, or consisting essentially of:
a) admixing
  1) a liquid and
  2) a complex comprising
    i) an organometallic compound wherein the organic component is cyclooctadiene and the metal is selected from the group consisting of Group 8 metals, Group 9 metals, Group 10 metals, and combinations thereof, to form a mixture thereof, and
b) incorporating the mixture into or onto beta zeolite.

The third embodiment is a process comprising, consisting of, or consisting essentially of:
contacting a hydrocarbon feed with a catalyst in a reaction zone under reaction conditions wherein said catalyst comprises:
a) a complex comprising
  i) at least one metal selected from the group consisting of Group 8 metals, Group 9 metals, Group 10 metals, and combinations thereof; and
  ii) an organic compound; and
b) a support component comprising a solid acid.

Other aspects, objectives, and advantages of the present invention will be apparent from the detailed description of the invention and the appended claims.

DETAILED DESCRIPTION OF THE INVENTION

In accordance with the present invention, the inventive composition comprises, consists of, or consists essentially of:
a) at least one metal selected from the group consisting of Group 8 metals, Group 9 metals, Group 10 metals, and combinations thereof;
b) a cyclooctadiene; and
c) beta zeolite.

In accordance with the present invention, the second embodiment of the present invention comprises, consists of, or consists essentially of:
a) admixing
  1) a liquid and
  2) a complex comprising
    i) an organometallic compound wherein the organic component is cyclooctadiene and the metal is selected from the group consisting of Group 8 metals, Group 9 metals, Group 10 metals, and combinations thereof, to form a mixture thereof, and
b) incorporating the mixture into or onto beta zeolite.

The Periodic Table referred to in this application is the IUPAC Periodic Table of the Elements.

The inventive composition and the catalyst employed in the inventive process comprises a complex containing at least one metal selected from the group consisting of Group 8 metals, Group 9 metals, Group 10 metals, and combinations thereof. A complex is defined as the species formed by the reaction of a metal atom or ion with ligands. A ligand is defined as an anion or molecule that forms one or more coordinate covalent bonds to metal ions.

The at least one Group 8, 9 or 10 metal can be selected from the group consisting of iridium, rhodium, platinum, nickel, cobalt, palladium, iron, ruthenium, osmium, and combinations of any two or more thereof. Preferably, the metal is iridium or platinum.

Generally, the metal is present in the catalyst composition in a weight percent in the range of from about 0.01 to about 10 weight percent, preferably in the range of from about 0.1 to about 5 weight percent and most preferably in the range of from 0.2 to 2 weight percent based on the total weight of the catalyst composition.

Any suitable organic compound can be used. Most preferably, this compound is cyclooctadiene.

The composition can further comprise a compound having the formula $R_3X$. Any suitable compound having the formula $R_3X$ can be used in the process of the present invention. Generally, "R" can be selected from the group consisting of hydrogen, an alkyl, an alkenyl, an alkynyl, cycloalkyls, cycloalkenyls, cycloalkynyls, aryls, substituted aryls, and substituted organic compounds. Generally, "X" is a Group 15 element selected from the group consisting of nitrogen, phosphorus, antimony, and bismuth. Preferably, the Group 15 element is phosphorus.

Preferably, the compound is an organophosphine. Preferred organophosphines include, but are not limited to, triphenylphosphine and tricyclohexylphosphine. The organophosphine can be a part of an organophosphine-containing compound. The $R_3X$ compound can bind to the metal and can become part of the complex.

The catalyst also includes a support component comprising a solid acid. Any solid acid can be used, including, but not limited to a zeolite, sulfated zirconias, acidic aluminas, chlorided alumina, non-zeolite aluminum/silicon compounds, aluminum fluoride, acid-washed clay, and combinations thereof. Preferably, the solid acid is a zeolite. Most preferably, it is beta zeolite (as defined in U.S. Pat. No. 3,308,069, the disclosure of which is incorporated herein by reference).

If a zeolite is used, it preferably has a constraint index (as defined in U.S. Pat. No. 4,097,367, the disclosure of which is incorporated herein by reference) of about 0.4 to about 12. Most preferably, it has a constraint index in the range of from 0.4 to 1.

The inventive composition and the catalyst employed in the inventive process can be prepared by a method comprising, consisting of, or consisting essentially of:

a) admixing
  1) a liquid and
  2) a complex comprising
     i) an organometallic compound wherein the organic component is cyclooctadiene and the metal is selected from the group consisting of Group 8 metals, Group 9 metals, Group 10 metals, and combinations thereof, to form a mixture thereof, and
b) incorporating the mixture into or onto beta zeolite.

In the inventive process, the catalyst can generally be prepared by admixing a liquid and a complex comprising an organic compound and at least one metal selected from the group consisting of Group 8 metals, Group 9 metals, Group 10 metals, and combinations thereof to form a mixture thereof. The term "admixing" as used herein, denotes mixing components in any order and/or any combination or sub-combination. Any suitable means for admixing the components can be used to achieve the desired dispersion of such components. Examples of suitable admixing include, but are not limited to, mixing tumblers, stationary shelves or troughs, Euro Star mixers, which are of the batch or continuous type, impact mixers, magnetic stirrers, mechanical stirrers, and the like.

The liquid can be any solvent capable of dispersing and/or dissolving a complex comprising at least one organic compound and at least one metal selected from the group consisting of Group 8 metals, Group 9 metals, Group 10 metals, and combinations thereof. Preferably, the liquid can be selected from the group consisting of water, light hydrocarbons, aromatics, alcohols, acetone, toluene and halogenated hydrocarbons. More preferably, the liquid is toluene or dichloromethane.

Any suitable organic compound can be used. Preferably, the organic compound is cyclooctadiene.

Any suitable compound having the formula $R_3X$ can also be used in the preparation of the catalyst for the inventive process. R is generally selected from the group consisting of hydrogen, an alkyl, an alkenyl, an alkynyl, cycloalkyls, cycloalkenyls, cycloalkynyls, aryls, substituted aryls, and substituted organic compounds. X is generally selected from the group consisting of nitrogen, phosphorus, arsenic, antimony, and bismuth.

Preferably, if an $R_3X$ compound is used, the compound is an organophosphine. Preferably, it is in the form of an organophosphine or in the form of one or more organophosphine-containing compounds. Preferably, the organophosphine is in the form of triphenylphosphine or tricyclohexylphosphine.

The mixture is added to the solid acid by means of incorporation.

A preferred method of incorporating is to impregnate using any conventional incipient wetness impregnation technique (i.e., essentially completely or partially filling the pores of substrate material with a solution of the incorporating elements) for impregnating a substrate. This preferred method uses an impregnating solution comprising the desirable concentration of the complex to ultimately provide the catalyst used in the inventive process. The amount of liquid that can be absorbed by the solid acid is determined by the following method:

To one-gram of the solid acid, the solvent is added drop wise until the liquid becomes visible around the particles. The required amount of solvent can be calculated by the weight difference. The complex is dissolved in exactly the amount of a suitable solvent that is required to fill all pores of the support. The solution is then added drop wise to the solid acid and then dried in a nitrogen stream, heat and/or under a vacuum.

If a single-step impregnation is not possible, then the process can be completed in several steps. The complex can be added to the solvent, the solvent is then added to the solid acid via incipient wetness, as described above, and the resulting substance is then dried. Then the process can be repeated until the desired amount of the complex is added.

In carrying out the inventive process, the reaction conditions in the reaction zone comprise a reaction temperature in the range of from about 100° C. to about 500° C. Preferably the reaction conditions include a reaction temperature in the range of from 200° C. to 350° C. Any suitable hydrocarbon feed can be used. Examples include, but are not limited to, alkanes with 2 to 10 carbon atoms per molecule. Preferably, the hydrocarbon feed is selected from the group consisting of normal pentane, isopentane, cyclopentane, cyclooctane or combinations thereof. Most preferably, it is a combination of isopentane and cyclooctane. Preferably, the inventive process is conducted in the absence of hydrogen.

The following example is presented to further illustrate the invention and is not to be considered as limiting the scope of the invention.

EXAMPLES

Example I

Zeolite beta (in the acid form), was impregnated with 0.1 grams of (triphenylphosphine)(cyclooctadiene)(pyridine)(iridium) hexafluorophosphate by incipient wetness. The iridium complex was dissolved in 3.5 grams of toluene. This solution was then added drop wise to 5 grams of zeolite beta extrudates and was dried with a purge of nitrogen.

A 3-gram quantity of the composition prepared above was placed in a stainless steel fixed bed reactor. The temperature was set to 258° C. under a nitrogen flow. A hydrocarbon feed was then introduced into the reactor. The outcome of this run was compared in Table I with a similar run using zeolite beta as a catalyst.

TABLE I

| Catalyst | Iridium Complex on Z-β Wt. % | Z-β Wt. % |
|---|---|---|
| Feed Component | | |
| C4 minus | 0.26 | 0.22 |
| iC5 | 88.55 | 88.56 |
| nC5 | 0.31 | 0.32 |
| cyC8 | 10.84 | 10.84 |
| C5 Olefin | 0 | 0 |
| C6+ (excluding CyC8) | 0.04 | 0.06 |
| Reactor Temp, ° C. | 258 | 316 |
| Products | | |
| C4 minus | 0.351 | 0.234 |
| iC5 | 80.76 | 88.10 |
| nC5 | 0.72 | 0.32 |
| cyC8 | 3.46 | 10.1 |
| C5 Olefin | 0.02 | 0.00 |
| C6+ (excluding CyC8) | 14.69 | 1.23 |

Z-β = zeolite beta
CyC8 = cyclooctane

As is evident from Table I, the isopentane conversion is greater using the iridium complex/beta zeolite catalyst than the run which uses zeolite beta alone as the catalyst.

While this invention has been described in detail for the purpose of illustration, it should not be construed as limited thereby, but intended to cover all changes and modifications within the spirit and scope thereof.

That which is claimed:

1. A method for making a composition comprising:
   a) admixing by incipient wetness;
      1) toluene; and
      2) (triphenylphosphine)(cyclooctadiene)(pyridine)(iridium) hexafluorophosphate;
   b) incorporating said mixture into or onto beta zeolite;
   c) drying said mixture with nitrogen; and
   wherein the method is conducted in the absence of hydrogen and the composition is capable of reducing the amount of $C_4$ and $C_5$ paraffins in a hydrocarbon feed in the reaction temperature range of 200° C. to 350° C.

* * * * *